United States Patent [19]

Reed

[11] Patent Number: 4,955,905
[45] Date of Patent: Sep. 11, 1990

[54] METHOD AND APPARATUS FOR MONITORING PRESSURE OF HUMAN TISSUE EXPANSION DEVICES

[76] Inventor: Andrew M. Reed, 7370 Taft Ct., Arvada, Colo. 80005

[21] Appl. No.: 371,523

[22] Filed: Jun. 26, 1989

[51] Int. Cl.$^5$ .............................................. A61F 2/12
[52] U.S. Cl. ......................................... 623/8; 623/14; 604/99
[58] Field of Search ....................... 623/8, 14; 604/99

[56] References Cited

U.S. PATENT DOCUMENTS

| | | | |
|---|---|---|---|
| 3,744,063 | 7/1973 | McWhorter et al. | 3/1 |
| 3,863,504 | 2/1975 | Borsanyi | 73/395 |
| 4,143,428 | 3/1979 | Cohen | 623/8 |
| 4,217,889 | 8/1980 | Radovan et al. | 128/1 R |
| 4,367,747 | 1/1983 | Witzel | 604/100 |
| 4,571,749 | 2/1986 | Fischell | 623/14 |
| 4,615,704 | 10/1986 | Frisch | 623/8 |
| 4,651,717 | 3/1987 | Jakubczak | 128/344 |
| 4,662,357 | 5/1987 | Pierce et al. | 128/1 R |
| 4,666,447 | 5/1987 | Smith et al. | 623/8 |
| 4,685,447 | 8/1987 | Iversen et al. | 128/1 R |
| 4,731,083 | 3/1988 | Fischell | 623/14 |

OTHER PUBLICATIONS

Neumann, C. G., "The Expansion of an Area of Skin by Progressive Distention of a Substaneous Balloon", *Plastic & Reconstructive Surgery*, vol. 19, No. 2, Feb. 1957, pp. 124–130.

*Primary Examiner*—Randall L. Green
*Assistant Examiner*—Stephanie L. Iantorno
*Attorney, Agent, or Firm*—John E. Reilly

[57] ABSTRACT

A pressure monitor for use in connection with tissue expander envelopes implanted beneath the tissue of the skin wherein a liquid is injected into the envelope to cause expansion of the skin or tissue and additional liquid is periodically injected to cause progressively increased expansion of the tissue. The tissue monitor includes means extablishing direct communication between the pressure monitor and the liquid injected under pressure whereby the monitor will provide a reading of the internal liquid pressure in the envelope. The method comprises the steps of implanting an inflatable envelope beneath the skin, injecting a sterile solution under pressure through a fill line communicating with the envelope, interrupting the flow of liquid under pressure into the envelope, sensing the pressure level of liquid injected into the envelope, and adjusting the pressure level when necessary either by removing from or injecting liquid into the envelope.

12 Claims, 1 Drawing Sheet

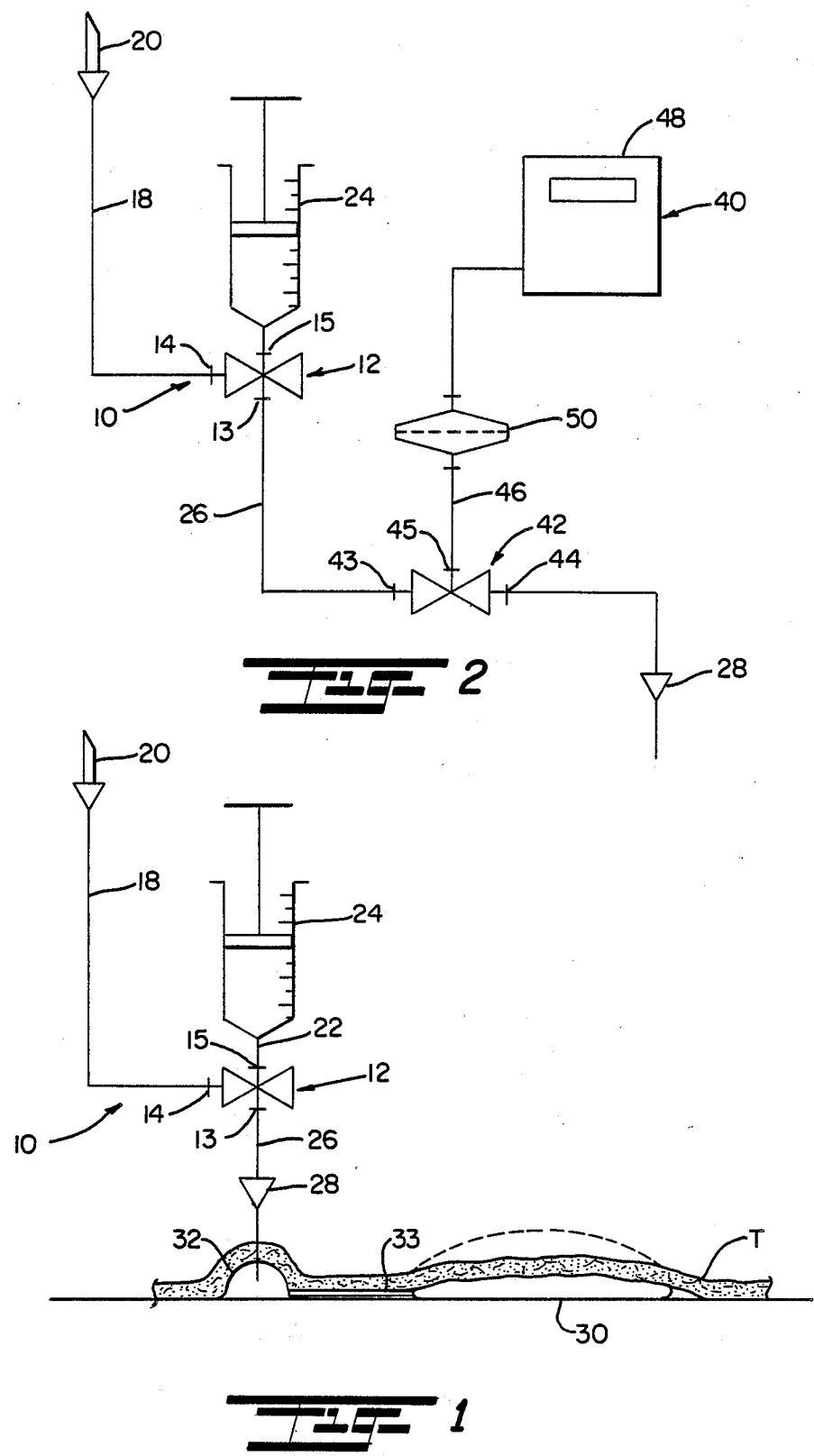

METHOD AND APPARATUS FOR MONITORING PRESSURE OF HUMAN TISSUE EXPANSION DEVICES

This invention relates to tissue or skin expansion devices; and more particularly relates to a novel and improved method and apparatus for the measurement and monitoring of the internal pressure of an implanted human tissue expander or inflatable breast prosthesis.

BACKGROUND AND FIELD OF THE INVENTION

Plastic and reconstructive surgery relies greatly on the use of free skin grafts, expansion of contiguous tissue or pediculed flaps of various shapes and sizes. In the repair of skin, the amount of skin available is often not sufficient for grafting and reconstruction. The requirement for additional skin or tissue has led to the development of various types of tissue expander devices. These devices are generally designed to cause gradual expansion of the skin and its subcutaneous tissue by applying progressively increasing pressure over a predetermined time period. An example of naturally occurring tissue expansion is seen in the extension of the skin over the pregnant female abdomen. A similar condition occurs when obese individuals undergo weight loss resulting in the development of folds of excess tissue.

Typically, the expander devices now commercially available and in use employ some form of elastic envelope or balloon which is surgically implanted under the skin and subcutaneous tissue in the area of the desired expansion. Ordinarily, a reservoir and connecting tube are implanted under the subcutaneous layers in communication with the envelope, and the envelope is slowly inflated by injecting a sterile saline solution into the reservoir using a syringe and hypodermic needle. The solution passes from the reservoir into the envelope through the connecting tube so as to inflate the envelope and cause it to exert pressure on the surrounding tissue which in turn expands to accommodate the increase in volume of the envelope. Periodic sterile injections of additional saline are typically performed at intervals of several days apart, this process being repeated until the desired degree of expansion has been achieved. When expansion has been completed, the envelope is surgically removed and the expanded tissue is then available for the desired plastic or reconstructive surgery. Representative tissue expander devices are set forth and described in a number of patents including U.S. Pat. No. 4,217,889 to C. Radovan; U.S. Pat. No. 4,666,447 to G. M. Smith et al; U.S. Pat. No. 4,615,704 to E. E. Frisch; U.S. Pat. No. 4,651,717 to E. R. Jakubczak; U.S. Pat. No. 4,662,357 to D. L. Pierce et al and U.S. Pat. No. 4,685,447 to A. A. Iversen et al.

Notwithstanding the development and availability of numerous types of tissue expander devices, a problem which is especially prevalent in connection with the use of these devices is that of closely controlling expansion of the tissue to avoid undue pain as well as tissue necrosis. For example, the aforementioned patent to Radovan et al describes the problems associated with too rapid expansion of tissue and which may lead to lack of blood flow in the surrounding expanded tissue which if not corrected results in tissue necrosis and loss of tissue viability. Similarly, wound dehissence may occur requiring a further healing period before expansion can be resumed. Presently, in the course of each filling or inflation procedure, the envelope is inflated until the tissue becomes "tight" or "firm" and this degree of tightness is based on the subjective opinion of the clinician; or, the clinician may gauge the degree of inflation by monitoring the pain experienced by the patient. However, this is not a reliable method as patients have widely variable thresholds of pain.

Pressure measuring devices have been utilized in the past for monitoring fluid pressure in the body. For example, U.S. Pat. No. 4,571,749 and U.S. Pat. No. 4,731,083 to R. E. Fischell disclose pressure measuring devices for a urinary sphincter. Similarly, U.S. Pat. No. 3,744,063 to D. M. McWhorter et al is directed to a method and apparatus for pressure monitoring an artificial sphincter. U.S. Pat. No. 3,863,584 to A. S. Borsanyi is concerned more with measuring the fluid pressure of plasma, blood or other fluids in the body while isolating the gauge from direct contact with the fluid. To the best of my knowledge, no one has recognized the ability to monitor tissue expansion by providing a reproducible method of measuring the pressure exerted on the tissue during or after the filling procedure. By closely monitoring the pressure and providing for a precise means of measuring actual pressure, it is possible to achieve an optimum inflation rate or degree of inflation which will overcome and avoid the previously noted problems associated with tissue expander devices. In this connection, it is hiqhly desirable that the pressure monitor be capable of directly sensing the fluid or liquid pressure condition of the tissue expander envelope but at the same time be isolated from the liquid such that the sterility of the fluid path is not compromised. That is to say that the liquid contents of the expander must be protected from any bacteria or particulate matter that may be carried by the liquid to or from the monitor itself. In this way, even though the tissue expander fill kit and tissue expander are disposable, the pressure gauge or monitor may be reusable.

SUMMARY OF THE INVENTION

Accordingly, it is an object of the present invention to provide for a novel and improved method and means for monitoring pressure of a skin or tissue expansion device so as to avoid tissue necrosis and/or pain associated with deliberate tissue expansion.

It is another object of the present invention to provide for a novel and improved pressure monitor conformable for use with various types of tissue expanders or breast prostheses which will enable quantification of the pressure exerted by the expander or prosthesis on the tissue or skin once implanted.

A further object of the present invention is to provide in a pressure monitoring device for tissue expanders for a novel method and means of maintaining sterility in the pressure monitor fluid path so that it can be reused; and further wherein a device is provided which is simplified in construction, easy to manufacture and readily adaptable for use with different commercially available tissue expanders or systems.

It is an additional object of the present invention to provide for a novel and improved method and means for accurately gauging the degree of inflation of an implanted tissue expander or breast prosthesis so as to avoid over-inflation, tissue necrosis and pain, and specifically to provide for a reusable pressure monitor in combination with a disposable tubing-filter set for connection of the monitor to the implanted expander while maintaining sterility of the fluid path.

In accordance with the present invention, a preferred form of pressure monitor has been devised for use in connection with tissue expander envelopes which are implanted beneath the tissue of the skin and wherein a liquid is injected into the envelope to cause expansion of the skin or tissue and additional liquid is periodically injected to cause progressively increased expansion of the tissue, the improvement comprising pressure monitor means including means establishing direct communication between the pressure monitoring means and the liquid injected under pressure into the envelope whereby the monitoring means will provide a reading of the internal liquid pressure in the envelope. The method of the present invention comprises the step of implanting an inflatable envelope beneath the skin, injecting a sterile solution under pressure through a fill line communicating with the envelope, interrupting the flow of liquid under pressure into the envelope, sensing the pressure level of liquid injected into the envelope, and adjusting the pressure level when necessary either by removing from or injecting liquid into the envelope.

The above and other objects, advantages and features of the present invention will become more readily appreciated and understood from a consideration of the following detailed description of preferred and modified forms of the present invention when taken together with the accompanying drawings in which:

BRIEF DESCRIPTION OF THE DRAWINGS

FIG. 1 is a schematic illustration of a conventional tissue expander device including an implanted reservoir, connecting tube and envelope in a deflated condition beneath the skin and subcutaneous tissue of a patient; and FIG. 2 is a schematic illustration of a preferred form of pressure monitoring device employed in combination with a conventional tissue expander device as illustrated in FIG. 1.

DETAILED DESCRIPTION OF THE PREFERRED EMBODIMENT

Referring in detail to the drawings, there is shown by way of illustrative example in FIG. 1 a tissue expander fill kit 10 which is merely representative of a number of commercially available devices for the same purpose. As shown diagrammatically in FIG. 1, the expander fill kit unit 10 is broadly comprised of a three-way stopcock 12 having valved ports 13, 14 and 15. The port 14 is connected to a reservoir supply line 18 and which may suitably be a length of plastic tubing which terminates in a universal spike or trocar 20. The spike 20 is adapted for connection into a reservoir or container of a sterile solution, not shown, and, for example, may be a sterile saline solution. Port 15 of the stopcock 12 is connected through line 22 to a conventional syringe 24. In turn, port 13 of the stopcock 12 is connected by a fill line or tubing 26 to a hypodermic needle represented at 28. Again, the device as described is representative of numerous types of conventional tissue expander fill kits and, for example, may be a Tissue Expander Fill Kit manufactured and sold by McGhan Medical Corporation of Santa Barbara, California.

In actual practice, as diagrammatically illustrated in FIG. 1, a deflated tissue expander envelope 30, self-sealing reservoir 32 and fill line 33 are implanted beneath the subcutaneous layers of skin and tissue represented at T. After implantation, the surgically induced wound is allowed to heal for a prescribed period of time. The stopcock 12 is then regulated to open the ports 14 and 15 while closing the port 13 in order to draw liquid from the source of sterile solution, not shown, via the line 18 into the syringe 24. After the desired amount of liquid is drawn into the syringe, the port 14 is closed and port 13 opened to permit the liquid to be advanced through fill line 26 and hypodermic needle 28. Once any entrapped air is removed from the fill line 26, the needle 28 is inserted into the subcutaneous reservoir 32 and liquid is then injected under pressure through the reservoir 32 and connecting tube 33 into the envelope 30 by continuing to advance the plunger of the syringe. The above described filling sequence may be repeated numerous times without the removal of the hypodermic needle 28 from the reservoir 32. Once the desired amount of liquid is injected, the needle 28 is removed from the reservoir 32 and the reservoir will seal itself to prevent any return flow of liquid out of the envelope. Filling of the envelope or balloon 30 will exert pressure on the surrounding tissue T which in turn expands to accommodate the increase in volume of the envelope. In accordance with conventional practice, filling of the envelope may continue over periodic intervals until the tissue becomes firm or the patient experiences pain. Subsequent sterile injections of additional solution are usually performed in office procedures by the clinician at intervals of four to seven days and the process is continued until the desired degree of expansion of the tissue has been achieved, as illustrated in dotted form in FIG. 1. Typically, the expansion of the tissue may require between eight and twelve weeks.

In accordance with the present invention, as shown in FIG. 2, a pressure monitor or gauge 40 is used in combination with the fill kit 10 of FIG. 1 to monitor pressure and regulate the rate of expansion of the envelope 30. To this end, the pressure monitoring unit 40 is comprised of a three-way stopcock 42 inserted into the fill line 26 including valved ports 43 and 44 in the line and a valved port 45 extending through line 46 into a pressure gauge 48. An in-line filter unit 50 is positioned in the line 46 to filter out bacteria or particulate matter without otherwise interfering with liquid flow through the line 46 into the pressure gauge 48. The balance of the system comprises the fill kit as illustrated in FIG. 1 and accordingly like parts are correspondingly enumerated.

The tissue expansion procedure is the same as described with reference to FIG. 1 in which the syringe is filled with solution from the line 18 with the port 13 closed and the other ports 14 and 15 are open. After the syringe is filled with the desired amount of liquid, port 14 is closed and port 13 opened together with ports 43 and 44 of the pressure monitoring unit; and the port 45 remains open long enough to fill the line 46 to the pressure gauge then is closed. Liquid is injected through the hypodermic needle 28 into the subcutaneous reservoir 32 until the overlying tissue is determined to have reached the desired firmness or degree of expansion. At this point, the port 13 is closed and port 45 opened to permit the liquid under pressure in line 26 to pass through into the line 46 so that the pressure level in the line may be measured by the gauge 48. The pressure gauge 48 may be a simple dial gauge of the desired range or a solid state electronic pressure monitor of a similar pressure range and which is compatible with the liquids typically used in tissue expansion procedures, such as, aqueous ionic fluids, especially saline. The in-line filter 50 has a sufficiently small pore size, on the order of less than 0.5 microns but more ideally of 0.2 microns or less, that liquid may pass freely therethrough but particulate matter and especially bacteria may not pass through the line. The filter device should be bidirectional so that it may be pressurized from both sides of the membrane and most desirably should be of low priming volume and minimal pressure drop.

Preferably, the fill kit as illustrated in FIG. 2 is disposable and can be supplied pre-sterilized including the bacterial filter 50. However, the pressure gauge 48 is not a single use or disposable device and therefore is a potential source of bacterial contamination. By positioning the filter 50 in the supply line 46 to the gauge 48, the passage of bacteria from the pressure monitor to the implanted expander is prevented and isolates the patient and expander from any bacteria present in the pressure monitoring equipment.

After each filling sequence, the internal pressure of the envelope can be read from the monitor 48 and which corresponds to the pressure exerted upon the surrounding tissue. If the pressure is less than desired, the filling sequence can be repeated. If the pressure is too high and thought to have the potential to cause tissue necrosis, saline solution may be removed directly from the envelope until the desired pressure is attained. In a similar manner, the pressure monitoring system may be used in the measurement of internal pressure of inflatable breast prostheses.

It will be evident that the invention may be used independently of a fill kit by connecting the stopcock 42 directly to a hypodermic needle 28. The port 43 remains closed and the needle is inserted directly into the reservoir 32 of the expander so that a direct measurement of the internal pressure may be made while maintaining sterility in the fluid line.

EXAMPLE 1

Medical grade injection tubing (Baxter Pharmaseal, Baxter Healthcare, Inc.) with male/female luer-lock connectors was connected to a 0.2 micron pore size cellulose acetate filter (Millex Millipore Corp., Bedford, Mass.) The male connector of the tubing was attached to an electronic pressure monitor. The battery-operated sensor had a digital liquid crystal display which covered 0 mm to 250 mm of Hg. pressure range (LCD evaluation board, SenSym, Inc., Sunnyvale, CA). Saline was isolated from the silicon transducer by using an in-line elastomeric diaphragm contained in a 13 mm filter holder (Swinnex Millipore Corp., Bedford, MA). The upstream side of the diaphragm between the transducer and the diaphragm was filled with silicone oil (Dow-Corning, Midland, MI).

To the second port of the 0.2 micron filter 50, a four-way disposable stopcock 12 was attached.

The remaining ports of the stopcock 42 were used to connect the device into the outward delivery tube 26 of a preassembled tissue expander fill kit, as shown.

The above apparatus was used to inflate a tissue expander over the pressure range of 0 mm to 250 mm of Hg.

EXAMPLE 2

A similar system to that described in Example 1 was constructed with a pressure monitor consisting of a dial pressure gauge 48 (Omega Engineering, Stamford, CT). Isolation of the gauge from the saline was not required as the saline contacting materials were compatible with ionic liquids, such as, saline.

This system was used to inflate and measure the internal pressure of a tissue expander but proved to be less accurate than the electronic pressure monitor described in Example 1.

EXAMPLE 3

A similar system to that described in Example 1 was constructed. However, the apparatus was not incorporated into a fill kit circuit.

The system was attached to a 21-gauge hypodermic needle 28 and used directly to measure the internal pressure of a tissue expander by insertion of the needle 28 into the expander reservoir 32.

In each of the Examples given, pressure readings were taken at the beginning and end of each filling sequence. Although pressure readings will necessarily vary with the size of the envelope, area of tissue to be expanded and age of patient, a typical pressure reading at the end of the first fill sequence may be on the order of 0 mm to 250 mm of Hg. By taking progressive pressure readings for a number of patients, it is possible to accurately determine the optimum pressure ranges and safety factor to be applied to prevent tissue necrosis and pain as the skin is expanded.

It is therefore to be understood from the foregoing that various modifications and changes may be made in the construction and arrangement of elements comprising the present invention as well as the particular sequence of steps followed in practicing the method of the present invention without departing from the spirit and scope of the present invention as defined by the appended claims and reasonable equivalents thereof.

I claim:

1. In apparatus for the expansion of skin tissue wherein an inflatable envelope is implanted beneath the skin and tissue to be expanded and a liquid is injected into said envelope to cause expansion of said skin and tissue, the improvement comprising:

a fluid pressure monitoring device, and sensing means connected to said pressure monitoring device for sensing the internal pressure of liquid injected into said envelope whereby to provide a pressure reading of the liquid injected into said envelope, said sensing means including a conduit extending between said pressure monitoring device and said liquid, and filter means in said conduit for filtering any particulate matter or bacteria carried in said liquid.

2. In apparatus according to claim 1, said pressure monitoring device being defined by a pressure gauge, said sensing means and filter means being disposable, single-use devices, and said pressure gauge being releasably connected to said sensing means for reuse independently of said sensing means and filter means.

3. In apparatus for expansion of human skin and underlying tissue wherein an inflatable envelope is implanted beneath the skin and tissue to be expanded and means are provided for injecting a liquid under pressure into said envelope, said injection means including a fill line and a hypodermic needle, the combination therewith comprising:

a pressure gauge, a flexible conduit interconnecting said pressure gauge and said fill line, a filter member in said conduit, and valve control means between said fill line and conduit to sequentially inject liquid under pressure into said envelope while maintaining said conduit in a closed position and opening said conduit for reading out the pressure level of liquid in said fill line by said pressure gauge.

4. In apparatus according to claim 3, said filter member having a porosity on the order of less than 0.5 microns.

5. In apparatus according to claim 3, including a syringe for injecting said liquid under pressure through said fill line, and a valve member between said syringe and fill line.

6. In apparatus according to claim 5, said valve control means defined by a three-way stopcock having first and second valve members interconnected to said fill line and a third valve member connected to said conduit.

7. In apparatus for the expansion of skin tissue wherein an inflatable envelope is implanted beneath the skin and tissue to be expanded and a liquid is injected into said envelope to cause expansion of said skin and tissue, the improvement comprising:
a fluid pressure monitoring device and means connected to said pressure monitoring device for sensing the internal pressure of liquid injected into said envelope whereby to provide a pressure reading of the liquid injected into said envelope, and means for injecting the liquid under pressure into said envelope having a fill line and a hypodermic needle, a three-way valve interconnecting said fill line and said pressure monitoring device, and valve control means for selectively opening and closing said three-way valve to sequentially inject liquid under pressure into said envelope and to enable reading of the pressure level in said liquid by said pressure monitoring device.

8. In apparatus according to claim 7, said three-way valve having first and second valved ports interconnected to said fill line and a third valved port connected to said pressure monitoring device.

9. The method of expanding human tissue comprising the steps of:
(a) implanting an inflatable envelope beneath the subcutaneous tissue layers of the skin;;
(b) injecting a sterile liquid solution under pressure through a fill line communicating with the envelope;
(c) providing a pressure level measuring device for measuring the pressure level of liquid injected into said envelope; and
(d) filtering out any bacteria present in said liquid between said fill line and said pressure level measuring device.

10. The method according to claim 9, repeating steps (b), (c) and (d) over periodic intervals until the tissue is expanded to the desired extent.

11. The method according to claim 9, including the step of adjusting the pressure level of liquid in said envelope either by removing or injecting liquid and thereafter measuring the pressure level of liquid in said envelope.

12. The method according to claim 9, in which step (d) is further characterized by connecting said pressure level measuring device to said fill line through a conduit containing a filter in said conduit for filtering out any bacteria carried in said liquid solution to or from said pressure level measuring device.

* * * * *